United States Patent [19]

Brenholdt

[11] Patent Number: 4,507,556

[45] Date of Patent: Mar. 26, 1985

[54] APPARATUS AND METHOD FOR DETERMINING PULP STOCK CONSISTENCY

[75] Inventor: Irving R. Brenholdt, Stratford, Conn.

[73] Assignee: St. Regis Paper Company, West Nyack, N.Y.

[21] Appl. No.: 448,040

[22] Filed: Dec. 8, 1982

[51] Int. Cl.³ .......................................... G01N 21/51
[52] U.S. Cl. ................................ 250/341; 250/354.1; 250/574; 356/342; 356/343; 356/338; 162/263
[58] Field of Search ................ 356/342, 343, 338; 250/432 R, 574, 575, 341, 354.1; 162/49, 263

[56] References Cited

U.S. PATENT DOCUMENTS

| | | |
|---|---|---|
| 1,701,331 | 2/1929 | Merrill . |
| 1,822,604 | 9/1931 | Simons et al. . |
| 2,083,074 | 6/1937 | Maass . |
| 3,110,172 | 11/1963 | Irwin . |
| 3,198,006 | 8/1965 | Williams . |
| 3,306,157 | 2/1967 | Hach ............................ 250/574 |
| 3,498,719 | 3/1970 | Wing et al. . |
| 3,518,003 | 6/1970 | Meyn . |
| 3,873,416 | 3/1975 | Forgacs et al. . |
| 3,892,485 | 7/1975 | Merritt et al. ................. 250/574 |
| 3,962,581 | 6/1976 | Zimmerman ................... 250/341 |
| 4,040,743 | 8/1977 | Villaume et al. ............... 162/263 |
| 4,062,226 | 12/1977 | Hietala . |
| 4,066,492 | 1/1978 | Hill ................................ 250/339 |
| 4,171,916 | 10/1979 | Simms et al. ................... 356/366 |
| 4,225,385 | 9/1980 | Hughes, Jr. et al. ........... 162/263 |
| 4,276,119 | 6/1981 | Karnis et al. ................... 356/342 |
| 4,278,887 | 7/1981 | Lipshutz et al. ................ 356/236 |
| 4,301,675 | 11/1981 | Wood et al. . |
| 4,318,180 | 3/1982 | Lundqvist et al. .............. 250/575 |
| 4,355,897 | 10/1982 | Kaye .............................. 356/342 |

Primary Examiner—Alfred E. Smith
Assistant Examiner—Carolyn E. Fields
Attorney, Agent, or Firm—Joseph M. Maquire

[57] ABSTRACT

An apparatus and method for determining the percentage of solid particles in a suspension (consistency) is provided. A source of diffused radiant energy is provided which energy is directed toward a suspension to be measured. The portion of the energy which is forward-scattered by the suspension is detected and a first signal indicative of the magnitude of the forward-scattered energy is produced. The portion of energy which is back-scattered by the suspension is detected and a second signal indicative of the magnitude of back-scattered energy is produced. The first and second signals are combined at a predetermined ratio to produce a feedback signal used to control the intensity of energy emitted from the radiant energy source. The intensity of energy emitted from the source is a function of the forward-scattered and back-scattered energy and is directly proportional to the consistency of the suspension being measured. By monitoring the power driving the radiant energy source, a display calibrated in terms of percent consistency can be provided.

20 Claims, 4 Drawing Figures

APPARATUS AND METHOD FOR DETERMINING PULP STOCK CONSISTENCY

BACKGROUND OF THE INVENTION

The present invention relates to an apparatus and method for determining the percentage of solid particles in a suspension ("consistency") and in particular to an apparatus and method for using diffused radiant energy to determine the consistency of paper pulp stock.

In paper manufacturing processes, the consistency of the pulp stock is a prime factor. For purposes of this disclosure the term "stock" is intended to mean wet pulp of any type at any stage in the paper manufacturing process. Different grades and weights of paper or paper products require different consistencies of stock. In addition, the consistency of pulp for a given paper product will depend on the process point at which a pulp sample is taken. The stock consists of the comminuted wood fibers, water, and sometimes certain additives. Such pulp stock is not a homogeneous mass, but rather is a mixture which contains the foregoing materials.

Since the consistency of the stock is of prime importance in the manufacturing of paper and paper products, it is highly desirable to know its consistency at all times. Further, in order to provide a reliable and high quality paper manufacturing operation, the consistency of unknown stock must be easily ascertained. Such a determination of consistency is particularly important when it is desired to switch a paper manufacturing apparatus from one grade of product to another. Such a grade change may necessitate the employment of stock having a different consistency.

The term "consistency" as used by the paper industry designates the concentration of pulp in water on a moisture-free basis. Consistency is expressed in terms of a percentage, with the percent consistency being calculated as follows:

$$\frac{\text{Moisture-free weight of pulp}}{\text{Weight of water and pulp}} \times 100 = \text{consistency (\%)}$$

In the pulp and paper industry, the consistency of stock may vary by three orders of magnitude, for example from 0.02% to 20%.

The direct measurement of consistency is presently accomplished by numerous techniques. With practice, a person can make a subjective estimate of consistency, using his eyes. An old viscosity method for determination of consistency is known as the "pencil" method. A calibrated tapered rod about 6 inches long is dropped from a vertical position a standard distance above the stock. A reading is taken of the depth to which the rod sinks into the stock. This technique is useful in a range of from about 2.5% to about 7% consistency.

Examples of other mechanical apparatus for determining consistency are shown in U.S. Pat. Nos. 3,110,172; 3,198,006; 4,062,226; 4,276,119; and 4,301,675.

Electrical consistency meters are also known which generally utilize the electrical resistance across the stock as a measure of the stock consistency. Such apparatus is disclosed in U.S. Pat. Nos. 1,701,331 and 2,083,074. In U.S. Pat. No. 1,822,604 a pulp freeness measurement is made by placing stock samples between the plates of a condensor and measuring the dielectric constant of the stock sample.

Consistency metering devices which rely on optical properties of stock are also known. In U.S. Pat. No. 4,318,180 the particle size distribution with respect to selected fraction classes in the direction of flow of a medium is measured by passing light through the medium and detecting the light transmitted therethrough. The detection of shives (i.e., splinters) in paper pulp is the subject of U.S. Pat. Nos. 4,066,492 and 4,225,385. In the '492 patent, multiple beams and multiple photodetectors are used to enable the measurement of "breadth" as well as "thickness" of the shive. Both photodetectors in the '492 patent detect transmitted light only.

U.S. Pat. Nos. 3,518,003 and 4,171,916 utilize polarized light for determining fiber concentration and consistency in paper stock. In U.S. Pat. No. 4,040,743 back-scattered, reflected, and transmitted energy is utilized to measure pulp slurry parameters. In this patent, an optical probe is disclosed which introduces light energy into a slurry, which energy is transmitted, back-scattered and reflected orthogonally. Separate electrical signals are provided which correspond to the back-scattered, reflected, and transmitted energy. The output corresponding to the back-scattered energy is divided by the log of the output corresponding to the reflected energy to produce a measurement of consistency which is independent of the pulp brightness.

U.S. Pat. No. 3,498,719 relates to a photoelectric consistency indicator for stock. Radiant energy is projected through a flowing sample and the amount of energy transmitted through the sample is detected by a photodetector. The sample is passed through a transparent tube constituting a lens having a given focal length. The photodetector is located at a point removed from the focal length to receive a low-resolution blurred image of the sample in transit. A second photodetector is directly illuminated and provides a reference for comparison with the response of the first photodetector. The two photodetectors are interconnected in an arrangement known as an electrical bridge, such that an electrical imbalance in the bridge is indicative of the consistency of the stock.

U.S. Pat. No. 3,962,581 discloses an infrared consistency meter wherein light from a low, constant power incandescent light source is reflected from the suspension flow stream, filtered to block passage of wavelengths less than 0.70 microns, and detected by a photocell. The apparatus can be configured to emphasize either a direct relationship between the photocell output and consistency changes or an inverse relationship thereof.

Each of the consistency meters or methods for determining consistency disclosed in the above patents can provide inaccurate results under certain conditions. Variables which can affect the accuracy of such consistency meters and methods are the type of pulp (e.g., long fiber bleached kraft, short fiber bleached kraft, short fiber unbleached ground wood), slurry flow rate, temperature, pulp freeness, pressure, ash content, and pH. It would be advantageous to provide an apparatus and method for measuring consistency which is linear through a wide range, e.g., from less than 0.01 through 15% consistency.

Through the use of diffused radiant energy, and the detection of forward-scattered and back-scattered energy in a suspension being measured, the present invention provides such an apparatus and method.

SUMMARY OF THE INVENTION

Apparatus for measuring the percentage of solid particles in a suspension is provided. The apparatus comprises a chamber adapted to contain a suspension to be measured. A radiant energy source is provided along with means for diffusing radiant energy from the source and introducing the diffused energy into the chamber. First sensor means is provided for sensing diffused energy in the chamber which is forward-scattered by a suspension therein and second sensor means senses diffused energy in the chamber which is back-scattered by a suspension therein.

In a preferred embodiment, the chamber is cylindrical and the first and second sensor means are mounted at diametrically opposed points along the circumference of the cylindrical chamber. The radiant energy source can emit infra-red energy, in which case the first and second sensor means detect infra-red energy.

One electronic control circuit which can be used in conjunction with the apparatus sums electrical outputs from the first and second sensor means at a predetermined ratio to produce a combined sensor output signal. This combined sensor output signal is compared to a reference signal by a comparator circuit which produces a difference signal indicative of the difference in magnitude between the combined sensor output signal and the reference signal. A variable power supply means is controlled by the difference signal and is coupled to the radiant energy source for energizing the source. Means can be provided to monitor the power delivered to the radiant energy source by the power supply means, in which case the monitoring means is calibrated to provide an indication of the percentage of solid particles in a suspension in the chamber based upon the magnitude of the monitored power.

The apparatus and method of the present invention provides an inherently broad range of linear operation from consistency near zero (0.01%) to consistency exceeding 10%. The measurement of consistency is independent of the color or brightness of the suspension being measured (e.g. paper pulp). The apparatus can be used either on-line (in the paper-making machinery) or off-line (e.g., with pulp samples retained in sealed glass or plastic bottles). Further, the system does not require highly coherent beams of radiation or the use of lenses, mirrors, prisms or other optically directive components which must be cleaned periodically or continuously. Finally, the apparatus and method is highly reliable and economical.

DESCRIPTION OF THE PREFERRED EMBODIMENT

The present invention introduces diffused radiant energy into a chamber containing a suspension to be measured. The suspension causes both forward-scattering and back-scattering of the diffused energy. Sensors are provided to detect such forward-scattered and back-scattered energy. An electronic circuit derives a feedback signal based upon the detected forward-scattered and back-scattered energy, which feedback signal is used to control the intensity of radiant energy that is introduced in a diffused manner into the chamber. The intensity of energy emitted from the radiant energy source is therefore a function of the forward-scattered and back-scattered energy and is directly proportional to the consistency of the suspension being measured. By measuring the power (e.g., electric current) which drives the radiant energy source, a measurement of the consistency of the suspension is obtained.

In pulp stock, radiant energy is scattered by pulp fibers and transferred forward, backward and obliquely through the stock by the medium of unbound water which typically exists up to a consistency of approximately 15%. The mechanism by which the radiant energy is scattered by the pulp fibers is known as "multiple scattering", which is any scattering of a particle or photon in which the final displacement is the sum of many displacements, usually small. The number of reflections of the radiant energy from fiber surfaces in the stock, and hence the transfer path length, is in non-linear proportion to consistency. The radiant energy lost by reflection from the stock to the walls of the chamber is also in non-linear proportion to consistency; hence the energy collected by a detector diametrically opposite from an energy source is in non-linear inverse proportion to consistency. Similarly, the energy scattered back from pulp fibers in the stock by way of the unbound water medium to a back-scattered radiation detector mounted adjacent the radiant source is in non-linear proportion to consistency. By combining the logarithmic equivalents of the detected forward-scattered and back-scattered energy, however, at a predetermined ratio as described hereinbelow, a linear measurement of consistency is achieved.

Figure 1:
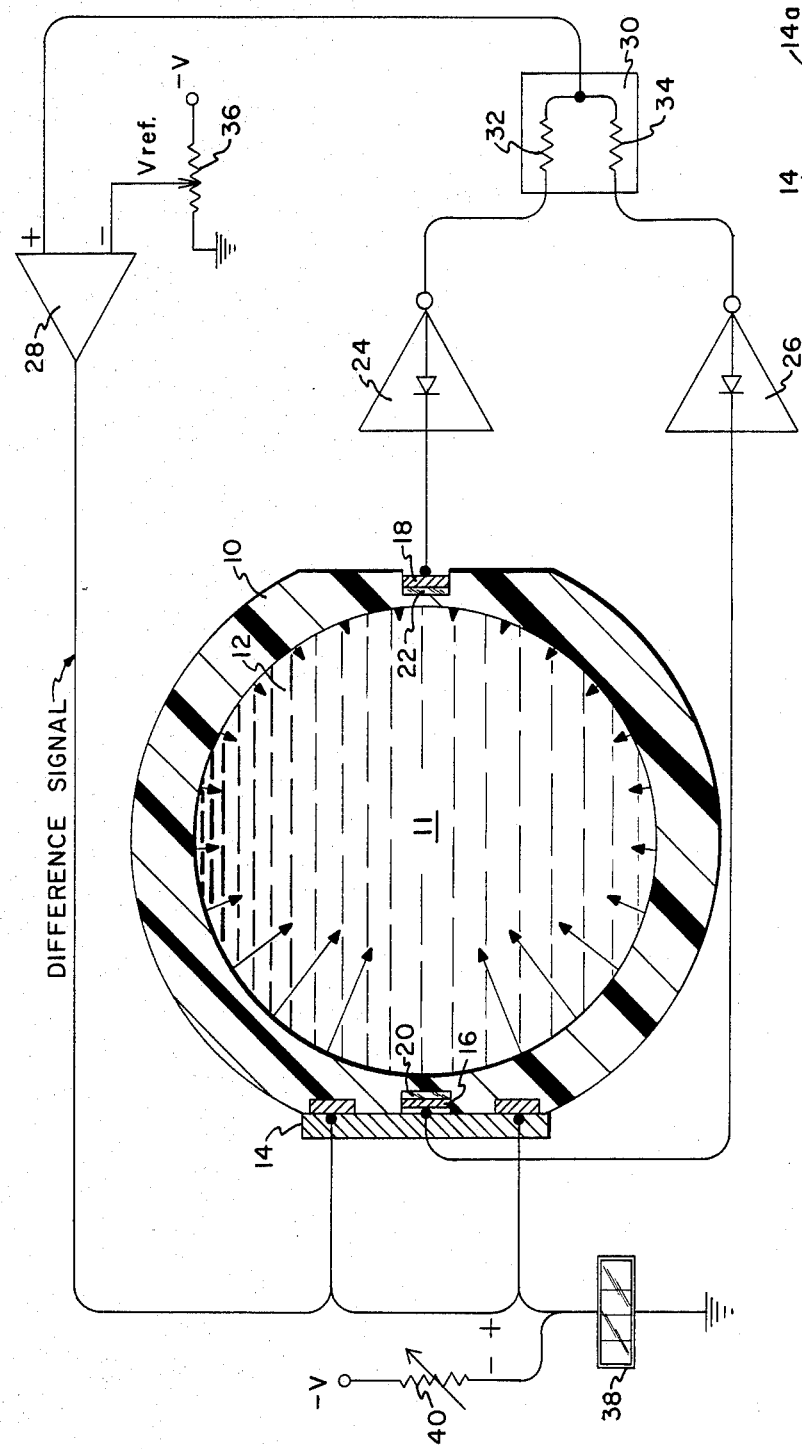
FIG. 1 is a system block diagram illustrating the apparatus of the present invention.

As shown in FIG. 1, the apparatus of the present invention includes a translucent cylinder 10 which can, for example, be fabricated of plastic. Translucent cylinder 10 defines a chamber 12 through which a suspension to be measured 11 (e.g., paper pulp slurry) can flow. In an alternate embodiment, chamber 12 is adapted to receive a glass or plastic bottle containing the suspension to be measured. In yet another embodiment, the apparatus can be configured so that chamber 12 can be dipped into a batch of paper pulp slurry for measuring the consistency thereof.

Figure 2:
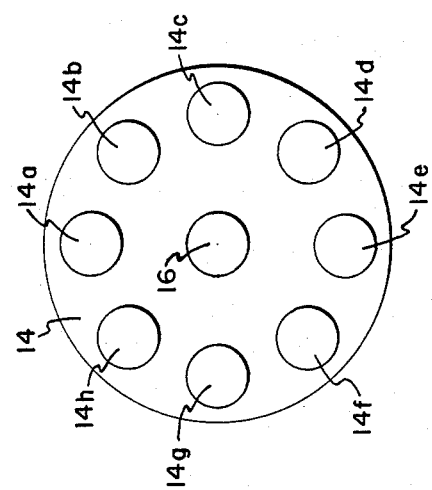
FIG. 2 is a cross-sectional view of a radiation emitter and sensor assembly in accordance with the present invention.

Mounted within the wall of translucent cylinder 10 is a radiant energy source, generally 14, which as shown in FIG. 2 can comprise a plurality of energy emitters 14a through 14h. In a preferred embodiment, radiant energy sources 14a through 14h comprise infra-red light emitting diodes (LED's) arranged in a circle as shown in FIG. 2. Mounted in the center of the circle formed by radiant energy emitters 14a through 14h is a radiation sensor 16. Sensor 16 is mounted along the axis of the path of radiation emitted collectively by radiant energy emitters 14a through 14h. A second radiation sensor 18 is mounted diametrically opposite radiation sensor 16.

In operation, energy emitted by radiant energy source 14 is diffused by translucent cylinder 10 so that a suspension 11 in chamber 12 is completely surrounded by radiant energy emitted by source 14. Those skilled in the art will appreciate that the magnitude of diffused energy will be greatest adjacent radiant energy source 14, and will decrease as the distance from source 14 increases, as indicated by the arrows shown in FIG. 1 which emanate from cylinder 10. Thus, the intensity of diffused radiant energy emitted into chamber 12 from translucent cylinder 10 will be greatest near radiation sensor 16, and will decrease as the energy travels, in a diffused manner, along translucent cylinder 10 toward radiation sensor 18. An important feature of translucent cylinder 10, which results from the diffusion of radiant energy, is that the entire volume of chamber 12 will be radiated by energy from source 14. In other words, radiation will be emitted throughout the entire circumference of translucent cylinder 10, but with the magnitude of radiation continuously decreasing as the distance from source 14 along the circumference increases. Thus, unlike prior art devices which used a point source or focused beam to measure particles in a suspension, the present apparatus enables the measurement of an entire sample. It is noted that when infra-red radiation is emitted from source 14, cylinder 10 does not have to be translucent to visible light. In fact, in such an instance cylinder 10 can be visibly opaque; as long as the cylinder is fabricated from a material which diffuses the infra-red radiation.

Optical filters 20 and 22 can be provided to exclude wavelengths shorter than a predetermined dimension, thereby excluding the detection of particulate matter in the suspension which is smaller than a specified size. For example, since pulp fiber diameters in paper pulp slurry range from 20 to 35 micrometers, optimum operation of the present apparatus can be achieved by using optical filters 20 and 22 that exclude wavelengths shorter than 20 micrometers.

When a suspension 11 to be measured is within chamber 12, the suspension will forward-scatter a portion of the energy from source 14 and back-scatter a portion of the energy from source 14. As the percentage of solid particles in the suspension increases (increased consistency) the amount of back-scattered radiation will increase and the amount of forward-scattered energy will decrease. As the percentage of solid particles in a suspension being measured goes down, the amount of forward-scattered energy will increase and the amount of back-scattered energy will decrease. Thus, at the theoretical outer limits, a suspension with a consistency of 100% will back-scatter all of the radiation and a suspension with a consistency of zero will not back-scatter any of the radiant energy from source 14.

Back-scattered radiation sensor 16 and forward-scattered radiation sensor 18 can comprise photodetectors which provide an output current proportional to the amount of radiation impinging thereon. Such photodetectors are well known in the art.

As shown in FIG. 1, the output of back-scattered radiation sensor 16 is coupled to logarithmic amplifier 26. Similarly, the output of forward-scattered radiation sensor 18 is coupled to logarithmic amplifier 24. Logarithmic amplifiers 24 and 26 serve to convert the electrical output signals from sensors 18 and 16 respectively to their logarithmic equivalents and also serve to amplify these signals. The converted, amplified signals are summed at a predetermined ratio by ratio network 30. Ratio network 30 comprises impedances 32 and 34. In a preferred embodiment, the ratio of impedance 32 to impedance 34 is $1:\pi^3$. The output of ratio network 30, which is a combined sensor output signal established by the summing of the outputs from logarithmic amplifiers 24 and 26 at a predetermined ratio, is coupled to the input of a comparator 28. The other input of comparator 28 is coupled to a reference voltage established by potentiometer 36. Comparator 28 provides a difference signal indicative of the difference in magnitude between the combined sensor output signal from ratio network 30 and the reference signal from potentiometer 36. This difference signal is fed back to control the intensity of energy emitted from radiant energy source 14. In FIG. 1, which is simplified for purposes of illustrating the invention, the difference signal from comparator 28 is used to energize or drive radiant energy source 14. The magnitude of the difference signal is directly proportional to the total radiant flux emitted by source 14 into chamber 12. The magnitude of the difference signal from comparator 28 is also directly proportional to the consistency of the suspension 11 present within chamber 12 due to the feedback arrangement of the electronic circuitry. Accordingly, by measuring the magnitude of the difference signal (which, in FIG. 1, is the signal which drives source 14) the percentage of solid particles (consistency) in a suspension 11 within chamber 12 can be determined. Meter 38 in FIG. 1 is calibrated to directly display such consistency. Potentiometer 40 is used to zero the meter 38 to correspond to a zero consistency within the chamber 12.

The system must be adjusted prior to initial use in order to calibrate the readings provided by display 38. In the preferred embodiment, it is desired to have display 38 directly indicate the percent consistency of a sample being measured. Initial adjustment is made by introducing a prepared sample (e.g., 5% consistency) into chamber 12 and adjusting potentiometer 36, which sets the reference voltage for comparator 28, until the display 38 reads 5.000. When an analog meter is used for display 38, potentiometer 36 is adjusted until the meter reads mid-scale. Then, a prepared water sample of zero percent consistency is introduced into chamber 12, and potentiometer 40 is adjusted until display 38 reads 0. Potentiometer 40 serves to negate the small residual current through display 38 attributable to a minimal radiation from source 14. After such calibration, the system is operable through a range from less than 0.01% to greater than 10% consistency.

It will be evident to those skilled in the art that due to the diffused nature of the radiation in chamber 12, which is present at least to some extent around the entire circumference of cylinder 10, a small amount of radiation may be back-scattered to forward-scattered sensor 18. Likewise, a small amount of radiation may be forward-scattered to back-scattered sensor 16. Any error attributable to such phenomenon will be eliminated by the calibration of the system as described above.

Figure 3:
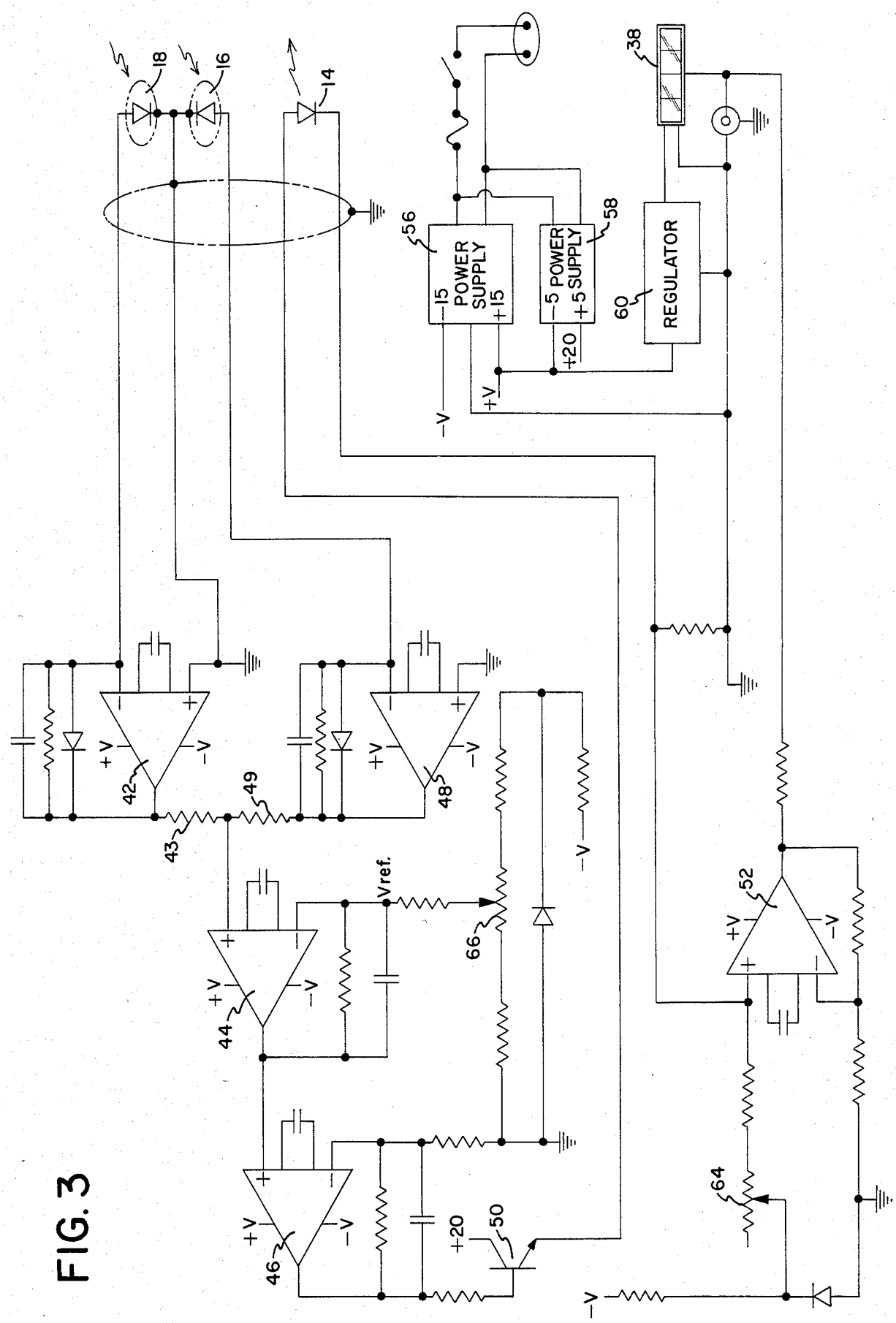
FIG. 3 is schematic diagram of electronic circuitry which can be used in conjunction with the present invention.

FIG. 3 is a detailed schematic diagram of an operating system which can be used with the apparatus of the present invention. Data generated by a system built and operated in accordance with FIGS. 1 through 3 is shown in graphical form in FIG. 4.

As shown in FIG. 3, a power supply 56 (15 volts) and power supply 58 (5 volts) supply power to the electronic circuitry. A 5 volt regulator 60 is used in conjunction with display 38, which is a digital readout meter. Current to drive light emitting diode 14 is provided by power output transistor 50. Light emitting diode 14 serves as a radiant energy source, and in a preferred embodiment comprises 8 identical LED's in series as shown in FIG. 2. Source 14 preferably emits energy in the infra-red range. Radiation sensors 16 and 18 detect back-scattered and forward-scattered radiant energy respectively and produce electrical signals indicative of the magnitude of detected energy. The outputs of radiation sensors 16 and 18 are connected to substantially identical, but separate amplifier circuits 48 and 42 respectively. The outputs of amplifiers 48 and 42 are summed at a predetermined ratio determined by resistors 49 and 43 to produce a "combined sensor output signal". In a preferred embodiment, resistors 43 and 49 form a ratio network having a ratio of $1:\pi^3$. Thus, for example, if resistor 43 is set at 10,000 ohms, resistor 49 will be set at 310,000 ohms. Also in a preferred embodiment, amplifiers 42 and 48 are logarithmic amplifiers.

The combined sensor output signal which appears at the junction of resistors 43 and 49 is fed to comparator amplifier 44. When the voltage at the positive input of amplifier 44 (the combined sensor output signal) becomes more negative than the reference voltage (V ref.) at the negative terminal of amplifier 44, the output current from transistor 50 (at the emitter terminal thereof) is lowered to reduce the radiation emitted from source 14. Thus, amplifier 46 and transistor 50 combine to form a variable power supply, controlled by the difference signal from comparator amplifier 44, to drive radiant energy source 14. The reference voltage applied to the negative input terminal of amplifier 44 is derived from calibration potentiometer 66 in a conventional manner. Potentiometer 66 in FIG. 3 is analogous to potentiometer 36 in FIG. 1. Amplifier 46 is coupled between amplifier 44 and output transistor 50 in order to drive the base of transistor 50.

Digital output meter or display 38 is driven by amplifier 52 which monitors the current flowing through radiation source 14. Calibration potentiometer 64 is coupled to the positive input of amplifier 52 to provide a means for zeroing digital meter 38 in a conventional manner. Potentiometer 64 is analogous to potentiometer 40 in FIG. 1. Those skilled in the art will note that the cathode terminal of source 14 is also coupled to the positive input of amplifier 52.

It will be appreciated that the circuit shown in FIG. 3 provides a negative feedback loop consisting of back-scattered radiation sensor 16, forward-scattered radiation sensor 18, logarithmic amplifiers 42 and 48, ratio network 43 and 49, comparator 44, amplifier 46, and transistor 50 which drives radiation source 14. The use of such a configuration provides a current through radiation source 14 which is directly proportional to percent consistency. By monitoring the power delivered to radiant energy source 14, digital meter 38, with proper calibration, provides an indication of the percentage of solid particles (consistency) of a suspension being measured. Radiant energy from source 14 is diffused, introduced into the suspension being measured, and scattered both forward and backward by the suspension depending on the consistency thereof. The back-scattered and forward-scattered energy is detected by radiation sensors 16 and 18 respectively.

The detection of both forward-scattered and back-scattered energy, along with the use of diffused radiation, provides a consistency meter with a linear output. The ratio established by resistors 43 and 49 facilitates linearization and extends the range of consistencies over which the apparatus can operate. Where the ratio established by resistors 43 and 49 is set at $1:\pi^3$, the consistency measurement can be expressed mathematically as:

$$\text{Consistency} = \frac{1}{\text{Log } S_F + (\text{Log } S_B/\pi^3)} - \frac{1}{K}$$

where $S_F$ represents the magnitude of forward-scattered radiation, $S_B$ represents the magnitude of back-scattered radiation, and K is the gain within the negative feedback loop.

In using the present invention to measure the consistency of paper pulp slurry, radiation source 14, back-scattered radiation sensor 16, and forward-scattered radition sensor 18 can be chosen to operate at infra-red wavelengths. In such a situation, radiation source 14 will typically peak at a wavelength of about 0.96 microns, and radiation sensors 16 and 18 will detect wavelengths of about 0.8 microns and above. Those skilled in the art will appreciate that other wavelengths and types of radiation can alternatively be used in system of the present design. The selection of radiation type and wavelength will be determined in part by the sizes of solid particles which are present in a suspension to be measured.

Figure 4:
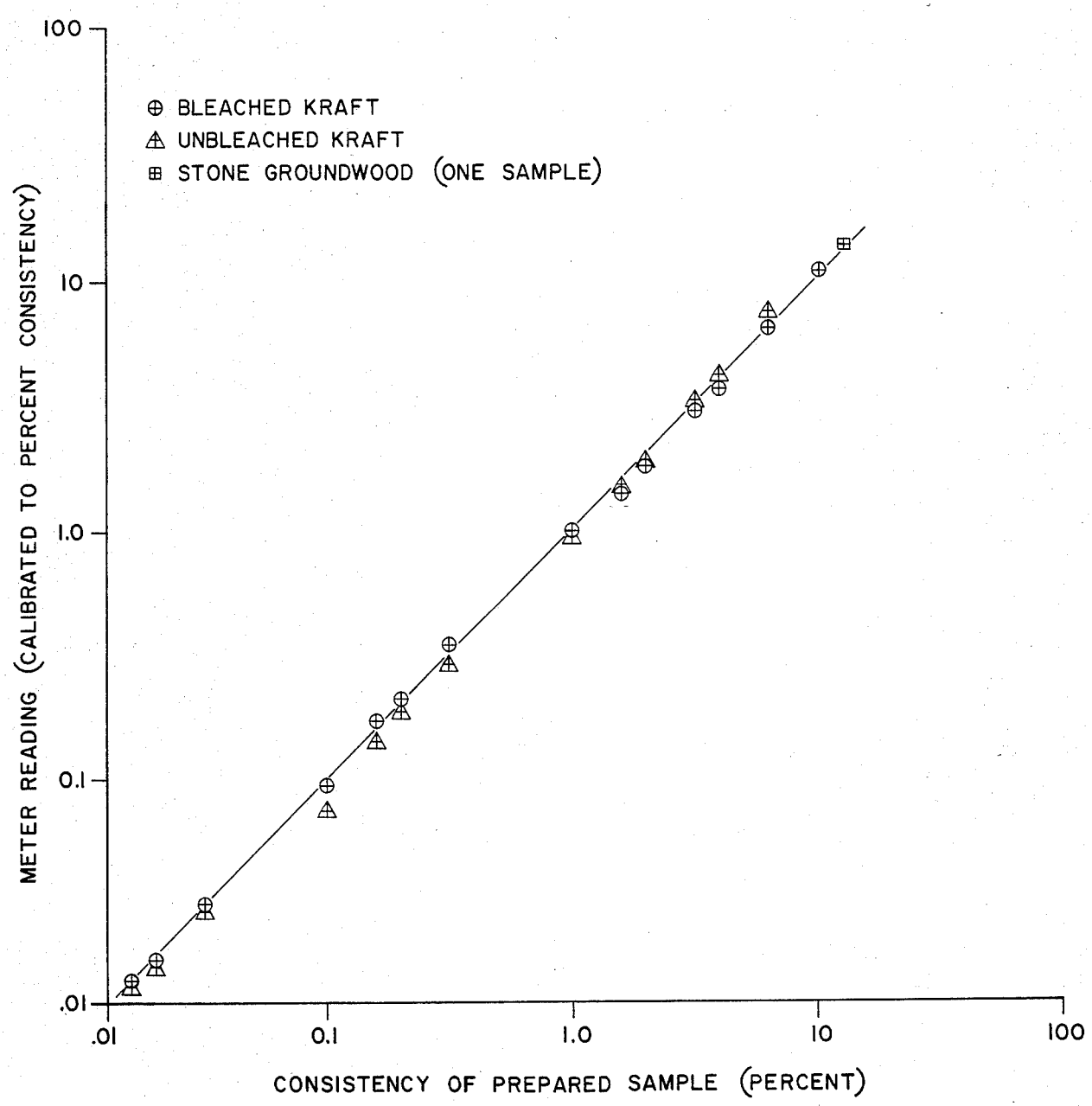
FIG. 4 is a graph of actual consistency measurements achieved with the apparatus and method of the invention.

The linearity of the present apparatus is illustrated in FIG. 4. FIG. 4 represents actual results of consistency measurements made with the present apparatus on three different types of paper pulp stock. The horizontal scale logarithmically plots the percent consistency of prepared samples which were measured. The vertical scale indicates, logarithmically, the actual meter readings achieved for the tested samples. The meter was calibrated, before the tests, to percent consistency. As shown, 14 samples of bleached kraft, 13 samples of unbleached kraft, and 1 sample of stone groundwood were tested. The accuracy of the present apparatus is such that a reading of zero is equivalent to ±0.002% consistency.

In operation, the present invention determines the consistency of a suspension by providing a source of diffused radiant energy and directing energy from the source toward a suspension to be measured. The portion of the energy which is forward-scattered by the suspension is detected and a first signal indicative of the magnitude of the forward-scattered energy is produced. The portion of energy which is back-scattered by the suspension is detected and a second signal indicative of the magnitude of back-scattered energy is produced. The first and second signals are combined at a predetermined ratio to produce a feedback signal which is used to control the intensity of energy emitted from the radiant energy source. The intensity of energy emitted from the source is therefore a function of the forward-scattered and back-scattered energy and is directly proportional to the consistency of the suspension being measured.

I claim:

1. Apparatus for measuring the percentage of solid particles in a suspension comprising:
   a chamber for containing a suspension to be measured;
   a radiant energy source;
   means for diffusing radiant energy from said source and introducing the diffused energy into said chamber;
   first sensor means for sensing diffused energy in said chamber which is predominantly forwarded-scattered when a suspension is present therein; and second sensor means for sensing diffused energy in said chamber which is predominantly back-scattered when a suspension is present therein.

2. The apparatus of claim 1 wherein said chamber is cylindrical and said first and second sensor means are mounted at diametrically opposed points along the circumference of said cylindrical chamber.

3. The apparatus of claim 1 further comprising:
means coupled to said first and second sensor means for producing an indication of the percentage of solid particles in a suspension in said chamber based upon the relative magnitudes of forward-scattered and back-scattered energy.

4. The apparatus of claim 1 wherein said radiant energy source emits infra-red energy and said first and second sensor means detect infra-red energy.

5. The apparatus of claim 1 further comprising:
means coupled to said first and second sensor means for summing the outputs thereof at a predetermined ratio to produce a combined sensor output signal;
comparator means for comparing said combined sensor output signal to a reference signal to produce a difference signal indicative of the difference in magnitude between said combined sensor output signal and said reference signal;
variable power supply means coupled to said comparator means for providing a variable output controlled by said difference signal;
means for coupling the output of said power supply means to said radiant energy source; and
means for monitoring the power delivered to said radiant energy source by said power supply means, said monitoring means calibrated to provide an indication of the percentage of solid particles in a suspension in said chamber based on the magnitude of the monitored power.

6. The apparatus of claim 5 wherein said radiant energy source emits infra-red energy and said first and second sensor means detect infra-red energy.

7. Apparatus for measuring the consistency of a suspension comprising:
a chamber for containing a suspension to be measured;
radiant energy source means for producing radiant energy to be introduced into said chamber for forward-scattering and back-scattering by a suspension;
a first radiation sensor for primarily sensing forward-scattered energy from said chamber;
a second radiation sensor for primarily sensing back-scattered energy from said chamber; and
electronic control means coupled to said first and second radiation sensors and said radiant energy source means for controlling the magnitude of radiant energy produced by said radiant energy source means, said control means providing a first electric signal proportional to said magnitude which is indicative of consistency.

8. The apparatus of claim 7 further comprising means for diffusing said radiant energy prior to its introduction into said chamber.

9. The apparatus of claim 8 further comprising display means coupled to receive said first electric signal and calibrated for displaying the percent consistency of a suspension in said chamber.

10. The apparatus of claim 8 wherein said radiant energy source means emits energy along a predefined path and said chamber is a cylinder formed from a material which diffuses energy introduced therein by said radiant energy source means, and wherein said first and second radiation sensors are mounted along the axis of said predefined path at diametrically opposed points on the circumference of said cylinder.

11. The apparatus of claim 8 wherein said radiant energy source means emits infra-red radiation, said apparatus further comprising first and second optical filtering means operatively associated with said first and second radiation sensors respectively for rejecting energy of wavelengths shorter than a predetermined value.

12. The apparatus of claim 8 wherein said first and second radiation sensors produce second and third electric signals indicative of the magnitude of the forward-scattered and back-scattered energy respectively, and wherein said electronic control means comprises:
means for summing said second and third electric signals at a predetermined ratio to produce a combined sensor output signal;
means for comparing said combined sensor output signal to a reference signal to produce a difference signal;
means for energizing said radiant energy source means; and
means for coupling said difference signal to said energizing means to control the magnitude of radiant energy produced by said radiant energy source means.

13. The apparatus of claim 12 wherein said first electric signal is produced by said energizing means and is used to energize said radiant energy source means; and said apparatus further comprises display means coupled to receive said first electric signal and calibrated for displaying the percent consistency of a suspension in said chamber.

14. The apparatus of claim 12 wherein said summing means comprises means for converting said second and third electric signals to their logarithmic equivalents and means for adding the converted second and third signals at a ratio of $1:(1/\pi^3)$.

15. The apparatus of claim 12 wherein said radiant energy source means comprises a plurality of infra-red emitters symmetrically arranged in a circle.

16. The apparatus of claim 15 wherein said second radiation sensor is mounted in the center of said circle, and wherein said first and second radiation sensors detect infra-red energy.

17. A method for determining the consistency of a suspension comprising:
providing a source of diffused radiant energy;
directing energy from said source toward a suspension to be measured;
detecting the portion of said energy which is predominantly forward-scattered by said suspension;
producing a first signal indicative of the magnitude of said predominantly forward-scattered energy;
detecting the portion of said energy which is predominantly back-scattered by said suspension;
producing a second signal indicative of the magnitude of said predominantly back-scattered energy;
combining said first and second signals at a predetermined ratio to produce a feedback signal; and
using said feedback signal to control the intensity of energy emitted from said source;
whereby the intensity of energy emitted from said source is a function of the forward-scattered and back-scattered energy and is directly proportional to the consistency of the suspension being measured.

18. The method of claim 17 wherein the predetermined ratio at which said first signal is combined with said second signal is $1:(1/\pi^3)$.

19. The method of claim 17 wherein said diffused radiant energy is infra-red energy.

20. The method of claim 17 wherein said source of diffused radiant energy is powered by an electric current and comprising the further step of:

displaying the consistency of the measured suspension on an electric meter coupled to monitor the current supplied to said source.

* * * * *